United States Patent [19]

Yamaguchi et al.

[11] Patent Number: 5,264,547

[45] Date of Patent: Nov. 23, 1993

[54] OPTICALLY ACTIVE ETHER LACTONE, OPTICALLY ACTIVE POLYMER THEREOF, AND PROCESS FOR PRODUCING THE POLYMER

[75] Inventors: Akio Yamaguchi; Yoji Hori; Susumu Akutagawa, all of Tokyo, Japan

[73] Assignee: Takasago International Corporation, Tokyo, Japan

[21] Appl. No.: 25,059

[22] Filed: Mar. 2, 1993

Related U.S. Application Data

[62] Division of Ser. No. 866,519, Apr. 10, 1992, Pat. No. 5,221,755.

[30] Foreign Application Priority Data

Apr. 12, 1991 [JP] Japan .................. 3-108738

[51] Int. Cl.$^5$ ............... C08G 63/08; C07D 321/08
[52] U.S. Cl. .................................. 528/354; 525/415; 528/357; 549/267
[58] Field of Search ........... 525/415; 528/354, 357; 549/237; 606/230, 231

[56] References Cited

U.S. PATENT DOCUMENTS

| | | | |
|---|---|---|---|
| 4,052,988 | 10/1977 | Doddi et al. .................. | 606/231 |
| 4,441,496 | 4/1984 | Shalaby et al. ................ | 606/230 |
| 4,470,416 | 9/1984 | Kafrawy et al. ............... | 606/230 |
| 4,920,203 | 4/1990 | Tang et al. .................... | 525/409 |
| 5,028,667 | 7/1991 | McLain et al. ................ | 525/415 |
| 5,208,297 | 5/1993 | Ford et al. ..................... | 525/415 |
| 5,221,755 | 6/1993 | Yamaguchi et al. ........... | 549/267 |

*Primary Examiner*—John Kight, III
*Assistant Examiner*—Shelley A. Dodson
*Attorney, Agent, or Firm*—Sughrue, Mion, Zinn, Macpeak & Seas

[57] ABSTRACT

An optically active 7-substituted-1,4-dioxepan-5-one derivative represented by the general formula (I):

wherein R represents an alkyl group having from 1 to 5 carbon atoms; and * means an asymmetric carbon atom, is disclosed. An optically active polymer represented by formula (II):

wherein R and * are as defined above; and n is an integer of 25 or more, obtained by ring opening polymerization of the optically active 7-substituted-1,4-dioxepan-5-one derivative represented by formula (I) is also disclosed. A process for producing the optically active polymer represented by formula (II) is further disclosed, comprising subjecting an optically active 7-substituted-1,4-dioxepan-5-one derivative represented by formula (I) to ring opening polymerization in the presence of at least one catalyst selected from the group consisting of (i) an organotin compound, (ii) an organoaluminum compound and water, and (iii) an organozinc compound and water.

5 Claims, 1 Drawing Sheet

OPTICALLY ACTIVE ETHER LACTONE, OPTICALLY ACTIVE POLYMER THEREOF, AND PROCESS FOR PRODUCING THE POLYMER

This is a divisional of application Ser. No. 07/866,519 filed Apr. 10, 1992 now U.S. Pat. No. 5,221,755.

FIELD OF THE INVENTION

The present invention relates to an optically active 7-substituted-1,4-dioxepan-5-one derivative and an optically active polymer obtained by the ring opening polymerization of the derivative, and to a process for producing the polymer.

The polyether-ester according to the present invention is a thermoplastic resin having optical activity, biodegradability (enzymatic degradability), biocompatibility, and hydrolyzability. Since this polymer is decomposable by the action of microorganisms present in a soil or water, it is a functional polymer extensively utilizable as a clean plastic which does not cause environmental pollution.

BACKGROUND OF THE INVENTION 1,4-Dioxepan-5-one of the formula (III):

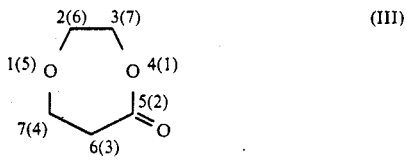

which corresponds to the basic skeleton of the compound of the present invention, is known (although the compound of formula (III) can also be named 1,5-dioxepan-2-one, only the former nomenclature is used throughout the specification and appended claims).

For example, British Patent 1,272,733 discloses a process comprising reacting ethylene glycol with acrylonitrile in the presence of 50% sodium hydroxide to obtain 2-(2-cyano ethoxy)ethanol and cyclizing this compound by passing dry hydrogen chloride therethrough in methylene chloride to prepare 5-imino-1,4-dioxepan-5-one hydrochloride, which is then heated in an aqueous solution at 40° C. to obtain 1,4-dioxepan-5-one (total yield: about 5%).

U.S. Pat. No. 4,470,416 discloses a process comprising reacting ethylene glycol with methyl acrylate in the presence of NaOMe (wherein Me is a methyl group, hereinafter the same) to prepare methyl 3-(2-hydroxyethoxy)propionate and converting this compound into 1,4-dioxepan-5-one using (i-PrO)$_4$Ti (wherein i-Pr is an isopropyl group) as a catalyst (total yield: about 17%). Further, Macromolecules, Vol. 22, 3832–3846 (1989) describes a process comprising reacting β-chloropropionyl chloride and ethylene in the presence of an AlCl$_3$ catalyst to prepare 1,5-dichloropentan-3-one and cyclizing this compound upon heating at 100° C. in the presence of H$_3$PO$_4$/NaH$_2$PO$_4$ to obtain 4-ketotetrahydropyran, which is then oxidized with 3-chloroperbenzoic acid to obtain 1,4-dioxepan-5-one (total yield: about 48%).

With respect to polymers of 1,4-dioxepan-5-one, the above cited U.S. Pat. No. 4,470,416 discloses that a copolymer of 1,4-dioxepan-5-one and lactide and/or glycolide is synthesized by use of tin caprylate and that the thus obtained polymer can be formed into fibers and used as a surgical suture and in other applications. U.S. Pat. No. 4,190,720 discloses a process for synthesizing a copolymer consisting of a large proportion of ε-caprolactone and a small proportion of 1,4-dioxepan-5-one in the presence of tin caprylate. However, any of the synthesis processes of 1,4-dioxepan-5-one disclosed in the above-cited patents is defective in that the yield is low. Further, these known processes are also disadvantageous in that polymers of the compound which can be produced are limited to copolymers and that since the monomer has no substituent group at the 7-position, the copolymers are not optically active and insufficient in biodegradability and, in particular, biocompatibility.

On the other hand, microorganisms which accumulate therein polymers of a 3-hydroxyalkanoic acid corresponding to a part of the constitutent components of the ring in the compound of the present invention have become known recently (see P. A. Holmes, *Phys. Technol*, 16, 32 (1985)). Since these polymers have advantageous properties such as biodegradability or enzymatic degradability, hydrolyzability, and biocompatibility, they are attracting attention as a new type of functional material (see *Seibunkaisei Kobunshi Zairyo*, p. 19, edited and written by Yoshiharu Doi, published by Kogyo ChosaKai, Japan, 1990). Further, ring opening polymerization of D-(+)-β-methyl-β-propiolactone is reported in *Polymer Letters*, 9, 173 (1970). However, since the above-described microbiological method utilizes a microorganism or an enzymatic reaction, it has various problems, such as the necessity of complicated steps, e.g., a step of separating the polymer from the microorganism and a step for optical resolution, and high production cost, leading to obstructing the commercial production thereof.

SUMMARY OF THE INVENTION

Under these circumstances, the present inventors have conducted intensive studies in order to overcome the above-described problems. As a result, it has been found that using as a starting material an optically active 3-hydroxyalkanoic acid ester produced by enantioselective hydrogenation of various β-ketoesters disclosed in JP-A-63-310847 (the term "JP-A" as used herein means an "unexamined published Japanese patent application"), a 7-substituted-1,4-dioxepan-5-one derivative having the structure of the starting ester as a skeleton in the molecule thereof, which is a novel cyclic ether-ester that has not been synthesized so far, can be obtained. It has also been found that this derivative readily undergoes ring opening polymerization to yield a corresponding optically active polyether-ester. The present invention has been accomplished based on these findings.

Accordingly, an object of the present invention is to provide a novel optically active 1,4-dioxepan-5-one derivative having a substituent group at the 7-position thereof.

Another object of the present invention is to provide a polymer having excellent biodegradability (enzymatic degradability), biocompatibility, and hydrolyzability.

Still another object of the present invention is to provide a process for producing the above-described polymer.

Other objects and effects of the present invention will be apparent from the following description.

In one aspect of the present invention, an optically active 7-substituted-1,4-dioxepan-5-one derivative represented by the general formula (I):

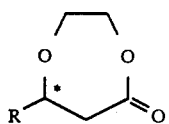

wherein R represents an alkyl group having from 1 to 5 carbon atoms; and * means an asymmetric carbon atom, is provided.

In other aspects of the present invention, an optically active polyether-ester obtained by ring opening polymerization of the above-described derivative and a process of production of the polymer are provided.

DETAILED DESCRIPTION OF THE INVENTION

Figure 1:
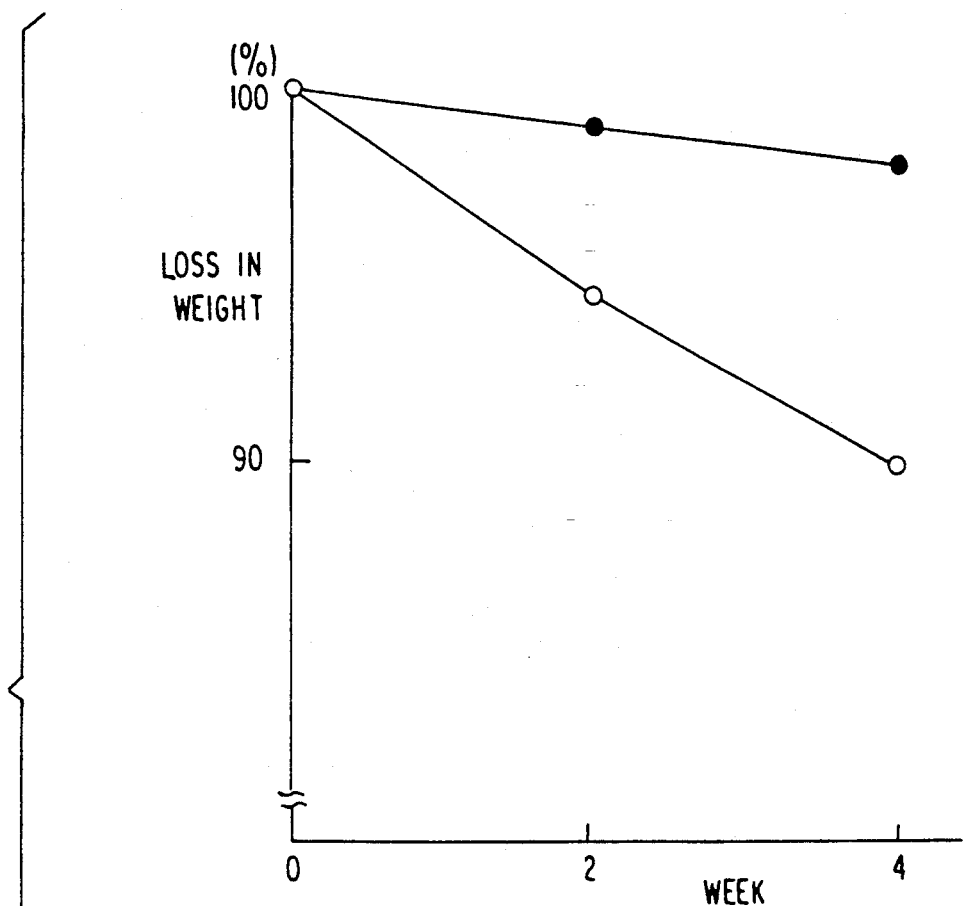
FIG. 1 is a graph showing a weight decreases in an active sludge comprising a polymer according to the present invention and commercially available polycaprolactone.
Figure 1:
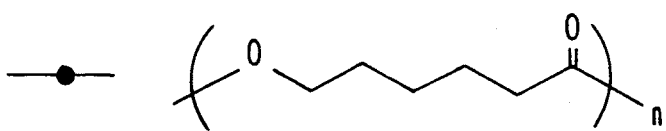
Figure 1:
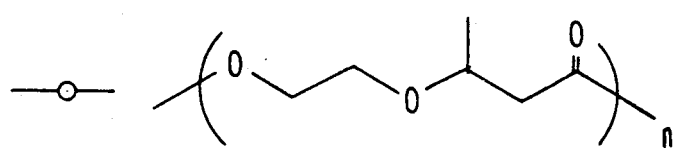

A process for producing the 7-substituted-1,4-dioxepan-5-one derivative of the present invention can be illustrated by the following reaction schemes:

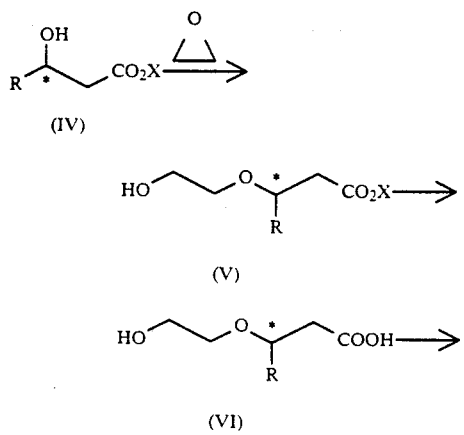

wherein R and * are as defined above; and X represents an alkyl group having from 1 to 6 carbon atoms.

The optically active 3-hydroxyalkanoic acid ester of formula (IV) used as a starting material in the above-described process can be easily obtained by the process disclosed in JP-A-63-310847. That is, a β-ketoester acid compound represented by the following formula:

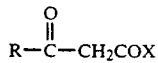

wherein R and X are as defined above, is subjected to enantioselective hydrogenation using as a catalyst an optically active ruthenium-phosphine complex, to give the desired ester (IV).

This optically active 3-hydroxyalkanoic acid ester (IV) is then reacted with ethylene oxide in the presence of a catalyst by blowing ethylene oxide into ester (IV) at atmospheric pressure and at a temperature between 80° and 100° C., or by allowing the reactants to react in an autoclave at a temperature between 80° and 100° C., to prepare a 3-(2-hydroxyethoxy)alkanoic acid ester having one mole of ethylene oxide added thereto, represented by formula (V). Examples of the catalyst used in this reaction include Lewis acids such as zinc chloride ($ZnCl_2$), chlorodiethylaluminum ($AlEt_2Cl$) (wherein Et is an ethyl group, hereinafter the same), chlorodimethylaluminum ($AlMe_2Cl$), and diethoxytrifluoroboron ($BF_3(OEt)_2$); and carbonium ions disclosed in JP-B-48-3810, such as tropylium tetrafluoroborate and triphenylmethylcarbonyl tetrafluoroborate. (The term "JP-B" as used herein means an "examined Japanese patent publication".) The amount of the catalyst used is sufficient to be 0.4% by weight or less.

The ester (V) is then hydrolyzed with ethanolic sodium hydroxide or potassium hydroxide to produce a carboxylic acid of formula (VI).

This optically active 3-(2-hydroxyethoxy)alkanoic acid ester is then reacted with ethyl chloroformate in a methylene chloride solvent using triethylamine as a base, whereby the optically active 1,4-dioxepan-5-one derivative of formula (I) can be obtained (William C. Agosta, *J. O. C.*, 39, 1607 (1974)).

Of the compounds represented by general formula (I), those wherein R represents an alkyl group having from 1 to 5 carbon atoms are novel.

An optically active polymer shown by formula (II) can be easily produced by ring opening polymerization of the optically active 7-substituted-1,4-dioxepan-5-one derivative of formula (I):

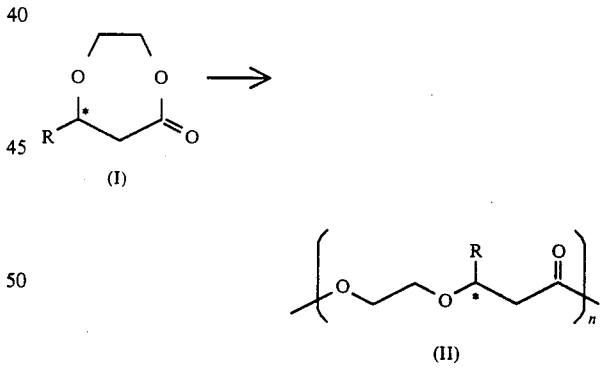

wherein R and * are as defined above; and n is an integer of 25 or more.

This ring opening polymerization can be carried out by dissolving the optically active 7-substituted-1,4-dioxepan-5-one derivative in an organic solvent such as hydrocarbons, e.g., toluene and benzene, introducing the solution into a reactor in an atmosphere of an inert gas such as nitrogen or argon, adding a catalyst thereto, and then polymerizing the derivative at atmospheric pressure and at a temperature between 60° and 110° C. for 30 minutes to 3 days.

Examples of the catalyst used include di-n-butyltin oxide, methylphenyltin oxide, tetraethyltin, hexaethyltin oxide, triethyltin methoxide, triethyltin ethoxide, tri-n-butyltin methoxide, tri-n-butyltin ethoxide, tin caprylate, a mixture of triethylaluminum and water (1/1 by weight), and a mixture of diethylzinc and water (1/0.6 by weight). They can be used alone or in combination of two or more thereof according to need. The catalyst is used in such an amount that the molar ratio of the catalyst to the monomer is in the range of from about 1/10 to 1/2,000.

As described above, according to the present invention, the novel 7-substituted-1,4-dioxepan-5-one derivative which is useful as an optically active monomer can be easily produced by an enantioselective synthesis reaction using as a starting material a 3-hydroxyalkanoic acid ester having high optical purity.

Polymers which are characterized by having optical activity, enzymatic degradability, hydrolyzability, and biocompatibility and, hence, are useful as new functional materials can be easily produced from the thus obtained monomer through a few of steps by an industrially advantageous process.

The present invention will be illustrated below in more detail with reference to the following Examples, but the invention is not construed as being limited thereto. Analytical instruments used in these Examples are as follows.

Nuclear magnetic resonance spectrometry (NMR): NMR Spectrometer Type AM-400 (400 MHz) (manufactured by Bruker Inc.); Internal standard: $^1$H-NMR: tetramethylsilane, $^{13}$C-NMR: tetramethylsilane.

Infrared absorption spectrometry (IR): IR Spectrometer Type IR-810 (manufactured by JASCO Inc.).

Molecular weight measurement: D-2520 GPC Integrator (manufactured by Hitachi, Ltd.).

Optical rotation measurement: Digital Polarimeter Type DIP-360 (manufactured by JASCO Inc.).

Mass spectrometry (MS): Mass spectrometer M-80B (manufactured by Hitachi, Ltd.).

Chemical purity measurement: Gas Chromatograph Type 263-80 (manufactured by Hitach, Ltd.; employing Silicone OV-101 (0.28 mm×25 m) as column. (The gas chromatography is hereinafter abbreviated as GC.)

EXAMPLE 1

Synthesis of R-(−)-7-methyl-1,4-dioxepan-5-one

Step 1

Preparation of methyl R-(−)-3-(2-hydroxyethoxy)-butyrate

A mixture of 118 g of methyl R-(−)-3-hydroxybutyrate and 0.4 g of tropylium tetrafluoroborate was heated to 80° C. with stirring, and ethylene oxide was then blown through the mixture at atmospheric pressure. While controlling the temperature of the mixture which was apt to rise at 80° to 100° C., 28 g of ethylene oxide was reacted therewith for 2 hours to obtain 146 g of a crude reaction product. This crude product was distilled to recover 64 g of the starting material and to obtain 27 g of the desired compound (having one mole of ethylene oxide added thereto) having a boiling point of 60° to 70° C./1 mmHg and a chemical purity, as measured by GC, of 91%. The percent yield was 36.4%.

$^1$H-NMR (400 MHz, CDCl$_3$) δ ppm: 1.22 (d, 3 H, J=6.2 Hz), 2.43 (dd, 1 H, J=15.8, 4.5 Hz), 2.58 (dd, 2 H, J=15.7, 8.4 Hz), 3.51 (m, 1 H), 3.68 (m, 3 H), 3.70 (s, 3 H), 3.98 (m, 1 H).

MS: m/z 162 (M+). [α]$_D$: −35.4° (c=1, CHCl$_3$, 20° C.)

Step 2

Preparation of R-(−)-3-(2-hydroxyethoxy)butyric acid

A mixture of 50 g of methyl R-(−)-3-(2-hydroxyethoxy)butyrate, 18.5 g of NaOH, 160 ml of ethanol, and 43 g of water was heated with stirring, and the mixture was reacted for 1 hour in a boiling state. After the reaction, the ethanol was distilled off under reduced pressure. To the residue were added 110 ml of water and 35.9 ml of hydrochloric acid to make the mixture acidic. Thereafter, water was distilled off under reduced pressure, and 200 ml of ethanol was added to the residue. This mixture was cooled and allowed to stand at 5° to 10° C. The precipitated sodium chloride was filtered out, and the filtrate was concentrated to obtain 45 g of the desired compound. The percent yield was 98.9%.

$^1$H-NMR (400 MHz, CDCl$_3$) δ ppm: 1.22 (dd, 3 H, J=18.0, 6.2 Hz), 2.49 (m, 2 H), 3.50 (m, 1 H), 3.70 (m, 1 H), 3.72 (m, 2 H), 3.97 (m, 1 H), 6.25 (m, 2 H).

MS: m/z 149 (M+).

[α]$_D$: −31.0° (c=1.6, CHCl$_3$, 20° C.).

Step 3

Preparation of R-(−)-7-methyl-1,4-dioxepan-5-one

A mixture of 29.2 g of R-(−)-3-(2-hydroxyethoxy)-butyric acid, 39.7 g of triethylamine, and 100 ml of methylene chloride was cooled with ice while stirring, and 25.7 g of ethyl chloroformate was added dropwise thereto at 10° to 15° C. The mixture was returned to room temperature and reacted for 3 hours. Subsequently, the reaction mixture was poured into 150 ml of water and extracted with CHCl$_3$. The CHCl$_3$ layer was washed successively with diluted hydrochloric acid and water, dried over anhydrous magnesium sulfate, and then concentrated to obtain 23 g of a crude product. The crude product was distilled under reduced pressure to obtain a fraction having a boiling point of 40° to 50° C./1 mmHg. This fraction was recrystallized from diethyl ether to obtain 13.6 g of pure R-(−)-7-methyl-1,4-dioxepan-5-one. This product had a chemical purity, as measured by GC, of 99.3% and a melting point of 46° C. The percent yield was 53.7%.

$^1$H-NMR (400 MHz, CDCl$_3$) δ ppm: 1.26 (dd, 3 H, J=8.3, 2.4 Hz), 2.72 (dd, 1 H, J=4.8, 0.8 Hz), 2.92 (dd, 1 H, J=14.9, 9.4 Hz), 3.83 (qdd, 2 H, J=14.3, 8.8, 0.6 Hz), 4.06 (ddd, 1 H, J=14.3, 3.9, 0.6 Hz), 4.22 (ddd, 1 H, J=13.6, 4.1, 0.5 Hz), 4.43 (dd, 1 H, J=13.7, 8.8 Hz).

$^{13}$C-NMR (100 MHz, CDCl$_3$) δ ppm: 22,26, 45.16, 69.25, 70.05, 70.80, 173.13.

MS: m/z 130 (M+).

IR: νmax (KBr) cm$^{-1}$: 2980, 2925, 2865, 1745, 1355, 1180, 1135, 1010.

[α]$_D$: −14.2° (c=1.0, CHCl$_3$, 20° C.).

EXAMPLE 2

Synthesis of R-(−)-3-(2-hydroxyethoxy)butyric acid polymer by ring opening polymerization of R-(−)-7-methyl-1,4-dioxepan-5-one Into an 80-ml reactor were introduced 1.30 g (10 mmole) of R-(−)-7-methyl-1,4-dioxepan-5-one, 0.0085 g (0.034 mmole) of dibutyltin oxide which had been dried at 100° C. for 24 hours under reduced pressure, and 5 ml of dry toluene. The mixture was stirred at 100° C. for 1 hour in a nitrogen atmosphere. The toluene was then distilled off under reduced pressure to obtain 1.235 g (percent yield: 95.2%) of the desired polymer (hereinafter abbreviated as PMDO).

$^1$H-NMR (400 MHz, CDCl$_3$) δ ppm: 1.21 (d, 3 H, J=6.2 Hz), 2.40 (dd, 1 H, J=15.4, 6.0 Hz), 2.61 (dd, 1 H, J=15.4, 7.1 Hz), 3.60-3.71 (m, 2 H), 3.90 (qdd, 1 H, J=6.2, 7.1, 6.0 Hz), 4.12-4.25 (m, 2 H).

$^{13}$C-NMR (100 MHz, CDCl$_3$) δ ppm: 19.84 (s), 41.75 (s), 63.79 (s), 66.67 (s), 72.68 (s), 171.20 (s).

IR cm$^{-1}$: 2975, 1735, 1380, 1305, 1260, 1190, 1090.

Weight average molecular weight ($M_w$): 86,600
Number average molecular weight ($M_n$) 60,300
$M_w/M_n = 1.44$.
$[\alpha]_D$: −24.6° (c=0.78, CHCl$_3$, 20° C.).

EXAMPLE 3

Synthesis of PMDO

Into an 80-ml reactor were introduced 1.30 g (10 mmole) of R-(−)-7-methyl-1,4-dioxepan-5-one and 0.0846 g (0.34 mmole) of dibutyltin oxide. The mixture was stirred at 110° C. for 50 minutes in a nitrogen atmosphere to obtain 1.30 g (percent yield: 100%) of PMDO.

$M_w$: 75,000, $M_n$: 45,000, $M_w/M_n = 1.67$.

EXAMPLE 4

Synthesis of PMDO

Polymerization was conducted in the same manner as in Example 1, except that 1.24 mg (0.005 mmole) of dibutyltin oxide was used as the catalyst and that the reaction was conducted for 72 hours. As a result, 0.42 g (conversion: 32.1%) of PMDO was obtained.

$M_w$: 6,750, $M_n$: 5,650 $M_w/M_n = 1.19$.

EXAMPLE 5

Synthesis of PMDO

Into an 80-ml reactor were introduced 1.30 g (10 mmole) of R-(−)-7-methyl-1,4-dioxepan-5-one, 0.1 ml (0.131 mmole) of an AlEt$_3$/H$_2$O catalyst (1/1 by weight) (1.31M toluene solution), and 20 ml of dry toluene. The mixture was stirred at 60° C. for 16 hours in a nitrogen atmosphere to obtain 1.23 g(conversion: 94.3%) of PMDO.

$M_w$: 39,900, $M_n$: 25,800, $M_w/M_n = 1.55$.

EXAMPLE 6

Synthesis of PMDO

Into an 80-ml reactor were introduced 1.30 g (10 mmole) of R-(−)-7-methyl-1,4-dioxepan-5-one, 1 ml (0.71 mmole) of an Et$_2$Zn/H$_2$O catalyst (1/0.6 by weight) (0.71M toluene solution), and 19 ml of dry toluene. The mixture was stirred at 100° C. for 48 hours in a nitrogen atmosphere to obtain 0.50 g (conversion: 38.8%) of PMDO.

$M_w$: 3,200, $M_n$: 1,900, $M_w/M_n = 1.63$.

EXAMPLE 7

Synthesis of R-(−)-7-ethyl-1,4-dioxepan-5-one

Step 1

Preparation of methyl R-(−)-3-(2-hydroxyethoxy)-pentanoate

According to the method described in *Jikken Kaqaku Koza*, Vol. 19, p. 441, 121 g of methyl 3-ketopentanoate was synthesized from 326 g of methyl acetoacetate and 189 g of propionyl chloride and then subjected to enantioselective hydrogenation using (+)-2,2'-bis[di(p-tolylphosphino)-1,1'-binaphthyl] tetrachlorodiruthenium-triethylamine [Ru$_2$Cl$_4$(T-BINAP)$_2$ Et$_3$N] according to the method disclosed in JP-A-63-310847, to obtain 110 g of methyl R-(−)-3-hydroxypentanoate. 100 g of this compound was treated in the same manner as in Step 1 of Example 1, to obtain 19 g of the desired compound having a boiling point of 60° to 65° C./1 mmHg and a chemical purity, as measured by GC, of 88.2%. The percent yield was 36.3%.

$^1$H-NMR (400 MHz, CDCl$_3$) δ ppm: 0.92 (t, 3 H, J=7.5 Hz), 1.58 (m, 2 H), 2.50 (m, 2 H), 2.64 (s, 1 H), 3.55 (m, 1 H), 3.60 (m, 1 H), 3.65 (m, 2 H), 3.70 (s, 3 H), 3.78 (m, 1 H).

$[\alpha]_d$: −29.6° (c=1, CHCl$_3$, 20° C.).

Step 2

Preparation of R-(−)-3-(2-hydroxyethoxy)pentanoic acid 48.6 g of methyl R-(−)-3-(2-hydroxyethoxy)pentanoate was treated in the same manner as in Step 2 of Example 1, to obtain 43.6 g of the desired compound. The percent yield was 99.7%.

MS m/z 162 (M+).

Step 3

Preparation of R-(−)-7-ethyl-1,4-dioxepan-5-one 15 g of R-(−)-3-(2-hydroxyethoxy)pentanoic acid was treated in the same manner as in Step 3 of Example 1, to obtain 10 g of the desired compound having a chemical purity as, measured by GC, of 99.0%. The percent yield was 26.4%.

$^1$H-NMR (400 MHz, CDCl$_3$) δ ppm: 0.98 (dd, 3 H, J=14.9, 7.4 Hz), 1.61 (m, 2 H), 2.76 (dd, 1 H, J=14.1, 1.1 Hz), 2.88 (dd, 1 H, J=14.8, 1.0 Hz), 3.59 (m, 1 H), 3.78 (ddd, 1 H, J=14.3, 8.9, 0.8 Hz), 4.08 (ddd, 1 H, J=14.3, 4.3, 0.6 Hz), 4.22 (ddd, 1 H, J=14.0, 4.3, 0.9 Hz), 4.42 (dd, 1 H, J=13.9, 8.8 Hz).

$^{13}$C-NMR (100 MHz, CDCl$_3$) δ ppm: 9.69, 29.22, 43.54, 69.38, 70.18, 75.77, 173.50.

MS: m/z 144 (M+).

IR: νmax cm$^{-1}$: 2975, 2950, 2880, 2860, 1742, 1358, 1180, 1020.

$[\alpha]_D$: −5.4° (c=1.4, CHCl$_3$, 20° C.).

EXAMPLE 8

Preparation of R-(−)-3-(2-hydroxyethoxy)pentanoic acid polymer 0.79 g of R-(−)-7-ethyl-1,4-dioxepan-5-one was treated in the same manner as in Example 2, to obtain 0.40 g (percent yield: 50.6%) of the desired polymer.

$^1$H-NMR (400 MHz, CDCl$_3$) δ ppm: 0.92 (t, 3 H, J=7.4 Hz), 1.56 (qd, 2 H, J=7.4, 5.9 Hz), 2.44 (dd, 1 H, J=15.4, 5.7 Hz), 2.56 (dd, 1 H, J=15.4, 7.2 Hz), 3.66-3.73 (m, 3 H), 4.13-4.24 (m, 2 H).

$^{13}$C-NMR (100 MHz, CDCl$_3$) δ ppm: 9.36 (s), 27.03 (s), 39.34 (s), 63.85 (s), 67.27 (s), 77.75 (s), 171.52 (s).

IR: (KBr) cm$^{-1}$: 2975, 1740, 1390, 1185, 1100.

$M_w$: 24,000, $M_n$: 9,900, $M_w/M_n = 2.42$.

$[\alpha]_D$: −14.4° (c=0.13, CHCl$_3$, 20° C.).

TEST EXAMPLE 1

Biodecomposition Test

Thin films (1 cm×1 cm, thickness 0.1 mm) of the polymer obtained in Example 2 and commercially available polycaprolactone having a molecular weight of 70,000 (comparative example) were each placed in 600 ml of a 500-ppm active sludge, and incubation was conducted with shaking at room temperature. Two weeks and four weeks after initiation of the incubation, each of the resulting films was weighed to determine the loss in weight (%). The results obtained are shown in FIG. 1.

While the invention has been described in detail and with reference to specific embodiments thereof, it will be apparent to one skilled in the art that various changes and modifications can be made therein without departing from the spirit and scope thereof.

What is claimed is:

1. An optically active polymer represented by formula (II):

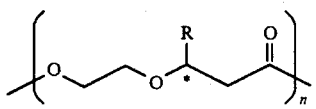

wherein R represents an alkyl group having from 1 to 5 carbon atoms; n is an integer of 25 or more; and * means an asymmetric carbon atom, obtained by ring opening polymerization of an optically active 7-substituted-1,4-dioxepan-5-one derivative represented by formula (I):

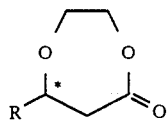

wherein R and * are as defined above.

2. A process for producing an optically active polymer represented by formula (II):

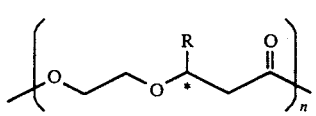

wherein R represents an alkyl group having from 1 to 5 carbon atoms; n is an integer of 25 or more; and * means an asymmetric carbon atom, which comprises subjecting an optically active 7-substituted-1,4-dioxepan-5-one derivative represented by formula (I):

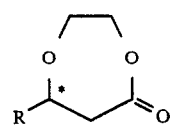

wherein R and * are as defined above, to ring opening polymerization in the presence of at least one catalyst selected from the group consisting of (i) an organotin compound, (ii) an organoaluminum compound and water, and (iii) an organozinc compound and water.

3. A process as claimed in claim 2, wherein said organotin compound is at least one member selected from the group consisting of di-n-butyltin oxide, methylphenyltin oxide, tetraethyltin, hexaethyltin oxide, triethyltin methoxide, triethyltin ethoxide, tri-n-butyltin methoxide, tri-n-butyltin ethoxide, and tin caprylate.

4. A process as claimed in claim 2, wherein said organoalumium compound is triethylaluminum.

5. A process as claimed in claim 2, wherein said organozinc compound is diethylzinc.

* * * * *